United States Patent [19]

Sallee

[11] Patent Number: 5,112,313
[45] Date of Patent: May 12, 1992

[54] IV COVER/PROTECTOR

[76] Inventor: Patricia L. Sallee, 2115 Yorktown Ct. S., League City, Tex. 77573

[21] Appl. No.: 673,260

[22] Filed: Mar. 20, 1991

Related U.S. Application Data

[63] Continuation-in-part of Ser. No. 393,401, Aug. 11, 1989, abandoned.

[51] Int. Cl.⁵ .......................... A61M 5/32; A61M 5/00
[52] U.S. Cl. ...................................... 604/180; 604/192
[58] Field of Search ...................... 604/174, 180, 192

[56] References Cited

U.S. PATENT DOCUMENTS

| | | |
|---|---|---|
| 3,722,508 | 3/1973 | Roberts . |
| 3,900,026 | 8/1975 | Wagner . |
| 3,901,226 | 8/1975 | Scardenzan . |
| 4,397,647 | 8/1983 | Gordon . |
| 4,517,971 | 5/1985 | Sorbonne . |
| 4,659,329 | 4/1987 | Annis . |
| 4,669,458 | 6/1987 | Abraham et al. . |
| 4,679,553 | 7/1987 | Proulx et al. . |
| 4,767,405 | 8/1988 | Lokken ............... 604/180 |
| 4,976,698 | 12/1990 | Stokley ............... 604/174 |

FOREIGN PATENT DOCUMENTS

| | | | |
|---|---|---|---|
| 8706474 | 11/1987 | PCT Int'l Appl. ............ | 604/174 |
| 2046095 | 11/1980 | United Kingdom ............ | 604/180 |

*Primary Examiner*—Randall L. Green
*Assistant Examiner*—R. Clarke
*Attorney, Agent, or Firm*—Kirk & Lindsay

[57] ABSTRACT

The present invention is directed to an intravenous needle protector which comprises a housing with a body and a terminating surface, at least one opening is in the body at the terminating surface for passage of the tubing which extends from the intravenous needle. The terminating surface extends from the body for the attachment of tape. The tape may be a part of the terminating surface or applied to that surface as well as to a person's body to hold the housing over the area of the intravenous needle injection. The body includes recedable retention means for retaining the needle. The body is preferably an oblong shape and has thin walls. The protector of the present invention is preferably produced as a plastic injected molded product out of such plastics as polyolefins such as polyethylene or polypropylene or other plastic materials such as polycarbonates.

17 Claims, 2 Drawing Sheets

IV COVER/PROTECTOR

This application is a continuation-in-part of application Ser. No. 07/393,401, filed Aug. 11, 1989 abandoned.

FIELD OF THE INVENTION

The present invention is directed to an IV cover or protector. The present invention is more particularly directed to a molded cover which is preferably made of a transparent plastic for easily covering an intravenous needle. The cover or protector may have a hinged cover so that when the protector has been taped in place that access to the needle may be obtainable without removing the cover/protector.

BACKGROUND AND PRIOR ART

Intravenous injections, as for administering blood transfusions, giving sera or plasma to patients and/or for feeding liquid nutrients to patients utilize intravenous needles of various sorts. In most instances, if any protective scheme has been used it has been a temporary partially protective scheme using available material such as a part of a styrofoam cup and held in place with adhesive tape. Such temporary schemes prevent the visual inspection of the needle or the area of the injection as well as requiring the untaping of the temporary protector to make certain of the well being of the patient and to make certain that the needle has remained in its proper place. Other temporary or permanent procedures have often attached the needle or the intravenous tubing to the device placing pressure or strain on the intravenous needle rather than merely providing protection to the needle and tubing. It is desirable to have a cover/protector which provides protection so that the patient may have movement of the limb, be able to roll over in bed and still provide visual inspection to the intravenous injection.

U.S. Pat. No. 3,900,026 discloses a guard for intravenous needles. The protective device is a transparent plastic enclosure with a neck element 17 which incorporates locking means to surround and hold the intravenous needle.

U.S. Pat. No. 3,901,226 discloses a protective guard for a hypodermic needle. The protective guard is formed of a flexible plastic material with a body portion having an intermediate notch therein so that the body portion may be bent about an intermediate axis to a variety of shapes.

U.S. Pat. No. 4,517,971 discloses a guard for protecting a venipuncture site and catheter retainer. This device has an openable cover or lid 20 which covers a base 16 which surrounds the venipuncture site. The base has a opening or window 48 which surrounds the venipuncture site. The intravenous tubing is threaded around two offset and integral hollow spools or annular cylindrical anchors 42 and 44. A cover 20 comes down over the tubing closing the venipuncture site.

U.S. Pat. No. 4,669,458 discloses a holder for securing and protecting an intravenous injection needle when the needle is inserted in the body of a patient. The holder includes a flat base having an adhesive bottom with an aperture in the middle of the base. A clear plastic window having an adhesive bottom is placed over the aperture on the base.

U.S. Pat. No. 4,679,553 discloses a venipuncture site protector. This protector has a body including a relatively rigid cup-like shield of frusto-pyramidal shape which is constructed of relatively thin, stiff but readily bendable material.

SUMMARY OF THE INVENTION

The present invention is directed to an intravenous needle protector which comprises a housing with a body and a terminating surface, at least one opening is in the body at the terminating surface for passage of the tubing which extends from the intravenous needle. The terminating surface extends from the body for the attachment of tape. The tape may be a part of the terminating surface or applied to that surface as well as to a person's body to hold the housing over the area of the intravenous needle injection. The body is preferably an oblong shape and has thin walls. The protector of the present invention is preferably produced as a plastic injected molded product out of such plastics as polyolefins such as polyethylene or polypropylene or other plastic materials such as polycarbonates.

In one embodiment of the present invention the body may have a hinged cover or roof so that access to the intravenous needle can be had without removing the tape which holds the housing to a person's body.

BRIEF DESCRIPTION OF THE INVENTION

The use of intravenous needles for injection of life support substances for all ages of person's is acknowledged. Intravenous injections for providing fluids, nutrients or medication is carried out on newly born infants, on patients in hospitals for all kinds of reasons, as well as the elderly in their homes or nursing homes. It is common to render immobile that portion of the person's body at which the injection is being made to prevent the danger either that the needle will be forced through the artery which may cause serious ramifications or that the needle may be pulled out of the person's body as a result of any accidental movement by the person or someone contacting the intravenous tubing.

To protect the person as well as the intravenous needle, the present invention provides a protector which when taped to the person in the area where the intravenous needle has been inserted into the artery of a person renders protection to the intravenous needle while permitting some mobility. The need for such a device was the result of a young person needing intravenous injections into the hand. When the arm of the young person was made immobile, the young person not being able to have use of their arm especially in attempting to turn over even when sleeping or to attempt any normal activities within the confines of a hospital bed, fought the restrictions to the arm and attempted to remove the intravenous needle. The protector of the present invention permits that mobility that will allow movement of the person and accidental contact of the area of the intravenous needle without contact of the needle itself through structure which encircles an adaptor juxtapositional to, recedable from, and retained by the protector. The protector also permits some accidental pulling on the intravenous tubing without the removal of the needle.

Figure 1:
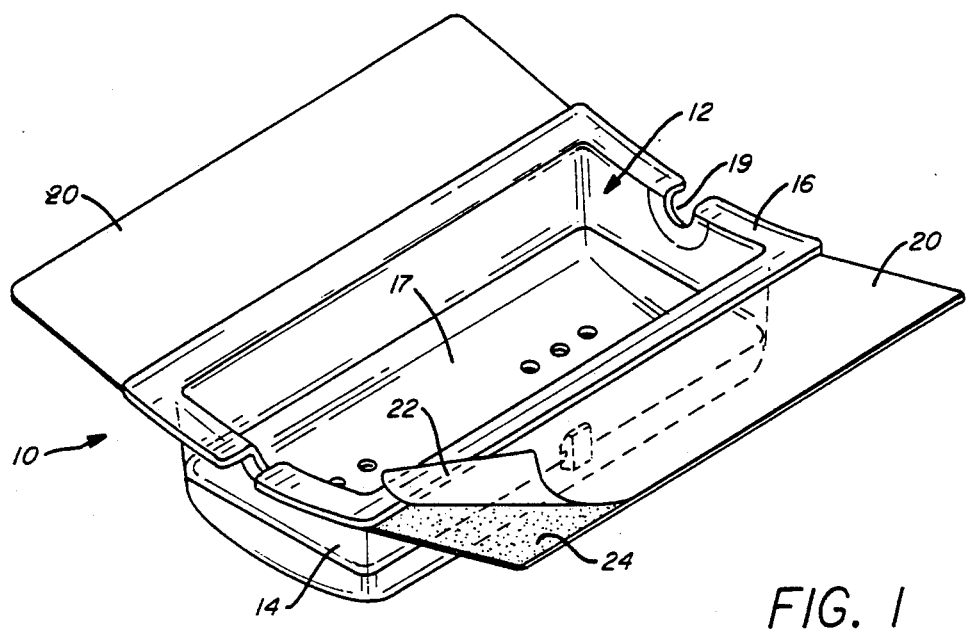
FIG. 1 is a isometric view of an intravenous needle protector of the present invention.

Referring to FIG. 1 which shows an intravenous needle protector of the present invention, an intravenous needle protector 10 has a housing 12 which includes a body 14 and a terminating surface 16.

The housing 12 preferably has a thin walled body 14 which provides a hollow interior 17. Preferably the housing 12 is an injected molded plastic product. The housing 12 may be formed from either a polyolefin such as polyethylene or polypropylene or other moldable plastics such as a polycarbonate. These plastics can form a transparent housing 12 so that one can see through the thin walled body 14 to the hollow interior 17.

The housing 12 is preferably oblong. The body 14 is oblong having a length less than three inches and a width less than two inches. The height of the body 14 is less than one inch. The body 14 may have a flat cover or roof or the cover or roof may be curved. The body 14 has at least one opening 19 at the terminating surface 16 midway the width dimension of the oblong body 14. The housing 12 may have another opening 19' midway of the other width dimension in the body 14 at the terminating surface 16. The openings 19 and 19' are to provide passageways for the tubing attached to the intravenous needle as will be described in more detail hereinafter.

The housing 12 has a terminating surface 16 which extends from the body 14. The terminating surface 16 may extend from all surfaces of the body 14, however, the terminating surface 16 preferably extends along the length dimension of the oblong body 14 with a sufficient surface dimension so that tape 20 may be applied to the terminating surface for holding the protector 10 to a person's body. In one embodiment of the present invention, the tape 20 is heat sealed to the terminating surface 16 and has a removable backing 22 for exposing the sticky surface 24 of the tape for application to a person's body. The tape 20 if sealed to the terminating surface 16 may be sealed to the top or bottom of the surface 16. However, adhesive tape normally used on person's skin may be applied or cut and stuck to the terminating surface 16 to secure the housing 12 to a person's body.

Figure 2:
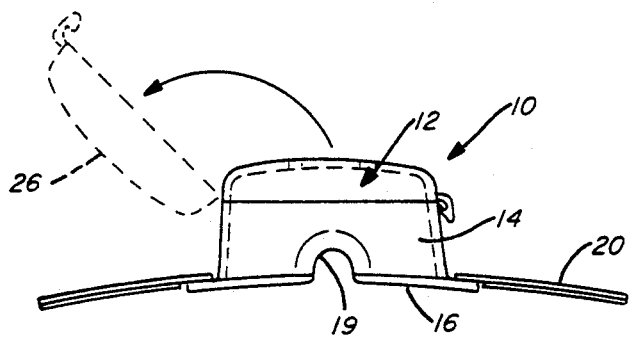
FIG. 2 is an end view of another embodiment of the present invention which shows that the intravenous needle protector may have a hinged top or roof.

Referring now to FIG. 2 wherein another embodiment of the protector 10 is shown. In this embodiment the housing 12 again has a body 14 with a terminating surface 16. The opening 19 in the body 14 at the terminating surface 16 is shown. The terminating surface 16 when viewed from the bottom may be slightly concave in that a slightly concave surface enhances securing the housing 12 when applied to a person's body. The tape 20 is shown in FIG. 2 secured to the top of the terminating surface 16. In this embodiment, the cover or roof 26 of the body 14 may be hinged so that the hollow interior 17 may be exposed without having need to remove the protector 10 from the person's body. A preferred plastic for this embodiment is polypropylene since the hinge may be extruded as part of the injection molded product. The roof 26 may have a latch 27 or some means to hold the roof closed.

Figure 3:
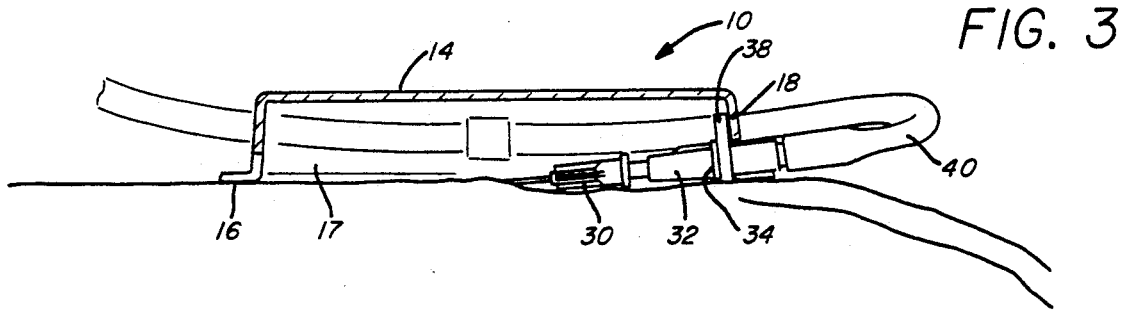
FIG. 3 is a cross-sectional view showing an intravenous needle and adaptor for connecting the tubing being covered by an intravenous needle protector of the present invention.
Figure 5:
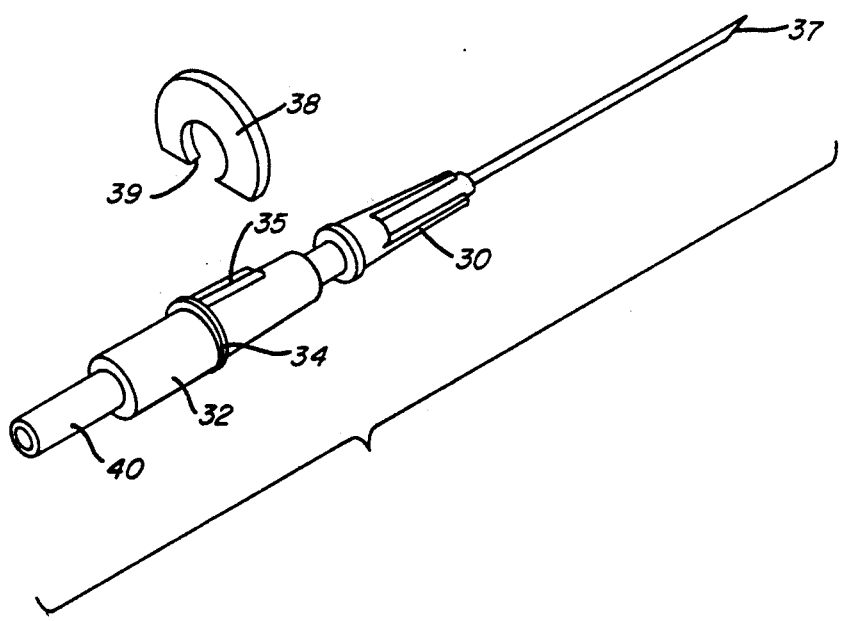
FIG. 5 is a standard intravenous needle and adaptor shown with a grommet which may be used so that the intravenous needle and adaptor cannot be withdrawn accidentally from the intravenous needle protector of the present invention.

The protector 10 of the present invention is shown covering a intravenous needle 30 in FIG. 3. The intravenous needle 30 is connected through an adapter 32 to intravenous tubing 40. The opening 19 in the body 14 of the protector 10 may have various sizes. The size is chosen so that the needle and adapter will not be removable in the event that the intravenous tubing 40 is accidentally pulled. The opening 19 may result in a friction fit between housing 12 and adaptor 32, bulb 42 or tube 40. However, it is preferable that there be a loose tolerance such that the juxtapositional adaptor 32, bulb 42, or tube 40 is retained yet recedable from the protector. This is advantageous in allowing housing 12 motion away from the needle tip 37 without the removal of same. It has been found that most adapters 32 have a ridge member 34 which is used to align the intravenous needle 30 and assuring that the needle is not rotated. This ridge member 34 can be used with a split grommet, which is described hereinafter, to maintain the intravenous needle 30 and the portion of the adapter 32 to which the needle 30 is attached within the protector 10. Reference is made to FIG. 5 which shows a needle 30 attached to an adapter 32 and then to intravenous tubing 40. The adaptor 32 has a ridge 34 with a marking 35 which aligns the position of the needle tip 37. A split grommet 38 having an opening 39 (which may be similar to or the same as opening 19) is placed behind ridge 34. As shown in FIG. 3, the split grommet 38 provides an enlarged surface so that the needle 30 and adaptor 32 cannot be removed from the housing 12 because the split grommet 38 cannot pass through the opening 19 and is securely held on the adaptor 32 by the ridge member 34. Grommet 38 may include a groove (not shown) around its outer circumference which would mate with wall 18 to fix grommet 38 in place around wall 18.

Figure 4:
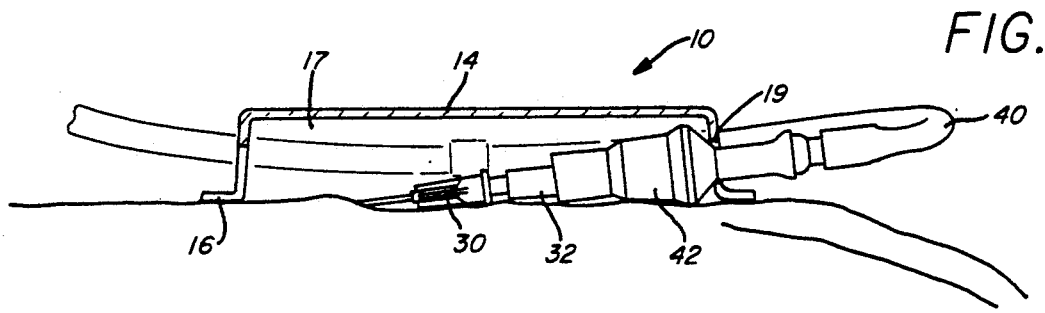
FIG. 4 is a cross-sectional view of another type of needle and adaptor for connecting the tubing used for intravenous injections which is covered by the intravenous needle protector of the present invention.

Referring now to FIG. 4 which discloses another type of adaptor including a bulb 42 used for connecting the intravenous needle to the tubing, a needle 30 is attached to tubing 40 through a adapter 32 encircled by a bulb 42. In some intravenous needle adapters, a bulb 42 is provided into which may be injected anti-coagulants such as heparin to make certain that the injected liquids are flowing properly In this embodiment of the adaptor the bulb 42 is sufficiently large such that it cannot be removed through opening 19. Hence, when the housing 12 is secured on a person's body such as their hand region, any accidental pulling of the tubing 40 will not remove the intravenous needle 30 from the housing 12.

Figure 6:
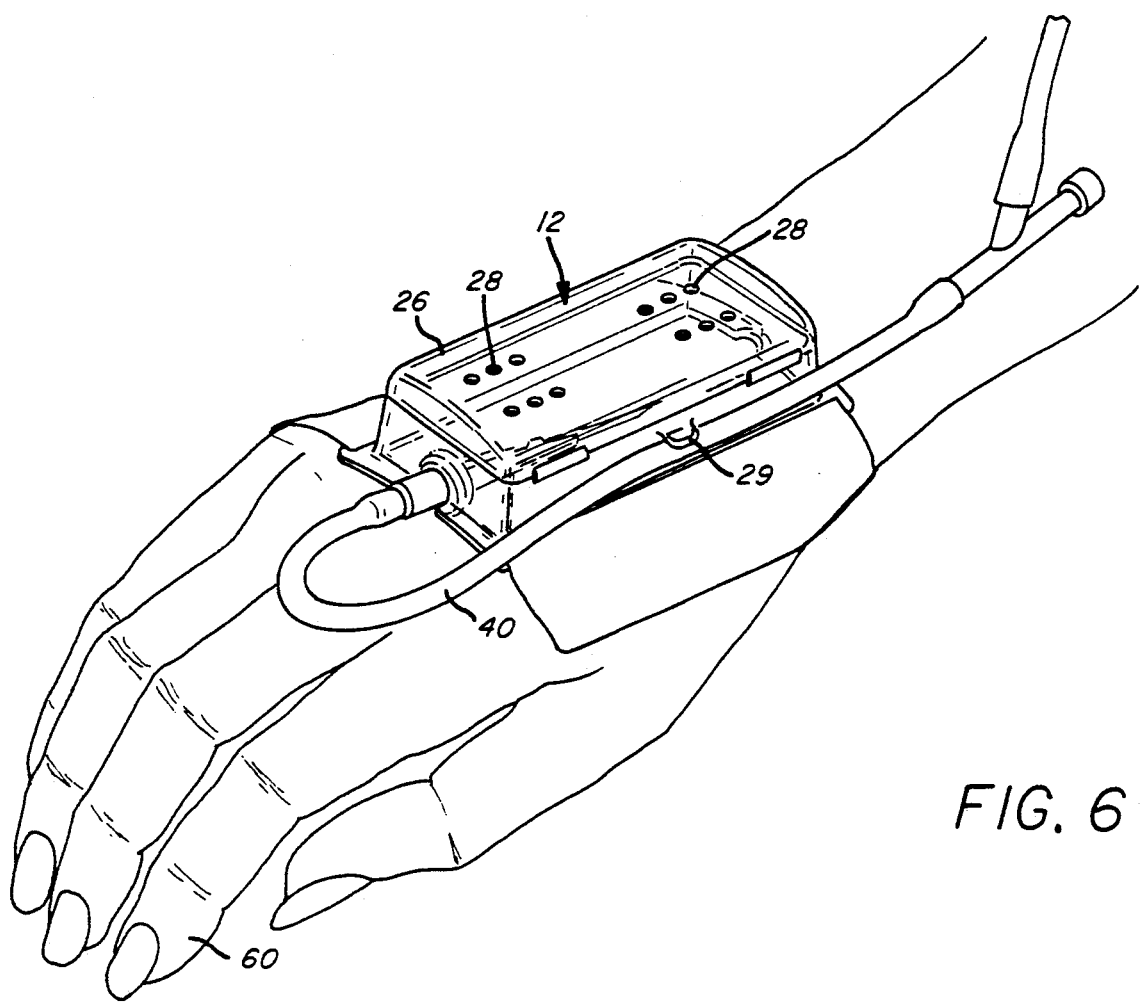
FIG. 6 is an isometric top view of the intravenous needle protector of the present invention as it would be applied on top of a person's hand.

Reference is had to FIG. 6 which shows the protector 10 on the top portion of a person's hand. It is noted that there may be openings 28 in the cover or roof 26 of the housing 12. These openings 28 provide air circulation to the hollow area 17 within the housing 12. It is also noted in FIG. 6 that the needle 30 is injected in the direction of the person's heart or the direction away from the person's fingers 60 and toward the arm 70. The tubing 40 therefore is first directed towards a person's fingers 60. Another feature of the housing 12 shown in FIG. 6 is that on the length side of the body 14 may be provided tubing holding means 29. The tubing holders 29 permit the tubing 40 to be looped and secured to the side of the body 14. The tubing holders 29 may be simply an upper and lower extension of plastic between which the tubing 40 is secured The roof or top 26 of housing 12 can be constructed with or from a magnifying material to act as a magnification device to enable one viewing the intravenous needle insertion site to easily check such site. The magnification will preferably be of a strength of times two (×2) or as needed.

Referring to FIGS. 3 and 6, grommet 38 can be constructed to be integral with the housing 12. In this construction opening 19 will be defined by integral grommet 38.

I claim:

1. An intravenous needle protector for the protection of a needle inserted into a body which comprises
    an adaptor extending from the needle;
    a housing with a body and a terminating surface;
        said body having at least one opening at said terminating surface for the passage of the adaptor extending from the needle;
        said terminating surface extending from said body sufficiently for attachment of tape means;
        at least two tape means attached to said terminating surface for holding said housing over the needle on a person's body; and
        recedable retention means encircling said adaptor and juxtapositional with respect to said opening which prevents withdrawal of the needle through said opening independent of rotation of the needle and which allows motion of said opening away from said adaptor.

2. A protector according to claim 1, wherein said body of said housing is thin walled.

3. A protector according to claim 1, wherein said body is oblong.

4. A protector according to claim 1, wherein said terminating surface extends from each surface of said body.

5. A protector according to claim 1, wherein said body has a length of less than 3 inches and a height of less than 1 inch.

6. A protector according to claim 1, wherein said body has a hinged roof which may be opened and shut.

7. A protector according to claim 1, wherein said body has tubing retaining means on at least one length of said body.

8. A protector according to claim 1, wherein said body is extruded from a clear plastic.

9. The protector according to claim 1, wherein said recedable retention means is a split grommet.

10. The protector according to claim 1, wherein said recedable retention means is a bulb.

11. The protector according to claim 1, wherein said recedable retention means is a ridge member.

12. The protector according to claim 1, wherein said body has at least one opening in a roof for air circulation.

13. The protector according to claim 1, wherein said body includes a means for magnification in a roof of said body.

14. An intravenous needle protector for the protection of a needle inserted into a body which comprises:
    an adaptor extending from the needle;
    a housing with a body and a terminating surface;
        said body having at least one opening in said terminating surface for passage of the adaptor extending from the needle;
        said terminating surface extending from said body sufficiently for attachment of tape means;
        at least two tape means attached to said terminating surface for holding said housing over the needle over a person's body; and
        a grommet encircling said adaptor and juxtapositional with respect to said opening to retain the needle within said body independent of rotation of the needle and to allow said adaptor to recede from said opening.

15. An intravenous needle protector for the protection of a needle inserted into a body which comprises:
    an adaptor extending from the needle;
    a housing with a body and a terminating surface;
        said body having at least one opening in said terminating surface for passage of the adaptor extending from the needle;
        said terminating surface extending from said body sufficiently for attachment of tape means;
        at least two tape means attached to said terminating surface for holding said housing over the needle over a person's body; and
        a bulb encircling said adaptor and juxtapositional with respect to said opening to retain the needle within said body independent of rotation of the needle and to allow said adaptor to recede from said opening.

16. The protector according to claim 14, wherein said body includes a means for magnification in a roof of said body.

17. The protector according to claim 15, wherein said body includes a means for magnification in a roof of said body.

* * * * *